US006198104B1

(12) United States Patent
Geagan et al.

(10) Patent No.: US 6,198,104 B1
(45) Date of Patent: Mar. 6, 2001

(54) RANDOMS CORRECTION USING ARTIFICIAL TRIGGER PULSES IN A GAMMA CAMERA SYSTEM

(75) Inventors: Michael J. Geagan, Wayne, PA (US); Michael J. Petrillo, Pleasanton, CA (US); Thomas E. Scharf, San Jose, CA (US); Donald R. Wellnitz, Pleasanton, CA (US)

(73) Assignee: ADAC Laboratories, Milpitas, CA (US)

( * ) Notice: Subject to any disclaimer, the term of this patent is extended or adjusted under 35 U.S.C. 154(b) by 0 days.

(21) Appl. No.: 09/178,036

(22) Filed: Oct. 23, 1998

(51) Int. Cl.[7] .................................................... G01T 1/166
(52) U.S. Cl. ................. 250/363.04; 250/363.03
(58) Field of Search ........................... 250/363.03, 363.04

(56) References Cited

U.S. PATENT DOCUMENTS

| | | |
|---|---|---|
| 4,071,761 | 1/1978 | Horrocks . |
| 4,181,855 | 1/1980 | Horrocks . |
| 4,418,282 | 11/1983 | Horrocks . |
| 5,285,073 * | 2/1994 | Schelten et al. ............ 250/394 |
| 5,296,708 | 3/1994 | Moyers et al. . |
| 5,444,252 | 8/1995 | Hug et al. . |
| 5,461,232 | 10/1995 | McCandless et al. . |
| 5,471,061 | 11/1995 | Moyers et al. . |
| 5,493,120 | 2/1996 | Geagan . |
| 5,552,606 | 9/1996 | Jones et al. . |
| 5,565,684 | 10/1996 | Gullberg et al. . |
| 5,585,637 | 12/1996 | Bertelsen et al. . |
| 5,608,221 | 3/1997 | Bertelsen et al. . |

(List continued on next page.)

FOREIGN PATENT DOCUMENTS 58-96269 * 6/1983 (JP) ........................ 250/363.03

OTHER PUBLICATIONS

Siu K. Yu and Claude Nahmias, "Single Photon Transmission Measurements In Positron Tomography Using $^{137}$Cs", McMaster Univ., Hamilton (ON), Jul., 1995, 29 pgs.

Karp, et al., "Singles Transmission in Positron Emission Tomography Using $^{137}$Cs", from IEEE Nuclear Science Symposium and Medical Imaging Conference Record, vol. 13, University of Pennsylvania and UGM Medical Systems (Philadelphia, PA), Oct., 1995, pp. 1363–1367.

(List continued on next page.)

*Primary Examiner*—Constantine Hannaher
(74) *Attorney, Agent, or Firm*—Blakely, Sokoloff, Taylor & Zafman, LLP (57) ABSTRACT

A technique for correcting for random coincidences in a gamma camera system is provided. The system includes a pair of scintillation detectors coupled to a processing system and is configured to detect radiation coincidences. Each detector generates trigger pulses in response to scintillation events to generate a plurality of event-based trigger pulses. Each detector includes a pulse generator, which generates a plurality of artificial trigger pulses. When an artificial trigger pulse in one detector occurs in coincidence with an event-based trigger pulse in the other detector, data is registered by the corresponding detectors, and the artificial trigger pulse is associated with a predetermined energy level. The data processing system examines the data to identify singles events that were registered as a result of artificial trigger pulses and prevents such singles events from contributing to the coincidence images. Instead, such singles events are used to generate a singles image for each detector. The singles images from the detectors are then used to create a randoms image, which is used to correct the coincidence images for random coincidences.

33 Claims, 10 Drawing Sheets

U.S. PATENT DOCUMENTS

| | | | |
|---|---|---|---|
| 5,646,408 | | 7/1997 | Goldberg et al. . |
| 5,834,779 | * | 11/1998 | Shao et al. ................ 250/363.03 |
| 5,841,680 | * | 11/1998 | Lightfoot ........................ 708/252 |
| 5,900,636 | * | 5/1999 | Nellemann et al. ......... 250/363.04 |
| 5,990,482 | * | 11/1999 | Bertelsen et al. ........... 250/363.04 |
| 6,008,493 | * | 12/1999 | Shao et al. .................. 250/363.04 |

OTHER PUBLICATIONS

P. Nellemann, et al., "Performance Characteristics of a Dual Head Spect Scanner With PET Capability", from IEEE Nuclear Science Symposium Conference Record vol. 3, ADAC Laboratories and UGM Laboratory, Oct., 1995, pp. 1751–1755.

Karp, et al., "Singles Transmission in Volume–Imaging PET with a $^{137}$Cs Source", *Phys. Med. Biol.,* vol. 40, May, 1995, pp. 929–944.

R.A. De Kemp, et al., "Design and Performance of 3D Photon Transmission Measurement on a Positron Tomograph with Continuously Rotating Detectors", International Meeting on Fully Three–Dimensional Image Reconstructioin in Radiology and Nuclear Medicine, Jul., 1995.

Robert Anthony Dekemp, B.A.Sc., Attenuation Correction Positron Emission Tomography Single Photon Transmission Measurement, Sep. 1992, McMaster Univ., Hamilton (ON), 106 pgs.

Bailey, et al., Ecart Art—A Continuously Rotating PET Camera: Performance Characteristics, Initial Clinical Studies, and Installation Considerations in a Nuclear Medicine Department, *European Journal of Nuclear Medicine,* vol. 24, No. 1, Jan. 1997, London (UK) and Knoxville (TN), 10 Pgs.

Robert A. De Kemp, et al., Attenuation Correction in PET Using Single Photon Transmission Measurement, *Med. Phys.,* vol. 21, No. 6, Jun. 1994, pp. 771–778.

G. Muehllehner, et al., "Performance Parameters of a Positron Imaging Camera," IEEE Transactions on Nuclear Science, vol. NS–23, Feb. 1976, pp. 528–537.

Gerd Muehllehner, Positron Camera with Extended Counting Rate Capability, *Journal of Nuclear Medicine,* vol. 15, No. 7, Jul. 1975, pp. 653–657.

Karp et al., Continuous–Slice Penn–PET: A Positron Tomograph with Volume Imaging Capability, *Journal of Nuclear Medicine,* vol. 13, No. 5, May 1990, pp. 617–627.

R.J. Smith et al., "Singles Transmission Scans Performed Post–Injection for Quantitative Whole Body PET Imaging," 1996 IEEE Nuclear Science Symposium Conference Record, vol. 3, Nov. 1996, Philadelphia (PA), 7 Pgs.

Karp, et al., Abstract No. 156 From proceedings of the 41st Annual Meeting, Scientific Papers, vol. 35, No. 5, Attenuation Correction in PET Using a Singles Transmission Source, May 1994, Philadelphia (PA), p. 41P.

G. Muehllehner, et al., Abstract No. 284, From proceedings of the 42nd Annual Meeting, Scientific Papers, SPECT Scanner with PET Coincidence Capability, *Journal of Nuclear Medicine,* Jun. 14, 1995, p. 70P.

James K. O'Donell, M.D., "Nuclear Medicine Camera Improves Image Quality and Patient Throughput", *Advance for Administrators in Radiology,* Aug. 1997, pp. 82–83.

Wong, W.H. et al., "A Scintillation Detector Signal Processing Technique with Active Pileup Prevention for Extending Scintillation Count Rates," IEEE Nuclear Science Symposium and Medical Imaging Conference, Albuquerque, New Mexico, Nov. 9–15, 1997, 5 pages.

Abstract, Wong, W.H. et al., "An Ultra–High Count–Rate Position Decoding and Energy Measuring Method for Cameras Using Anger Logic Detectors", 1997 IEEE Nuclear Science Symposium and Medical Imaging Conference, Albuquerque, New Mexico, Nov. 9–15, 1997, p. 88.

Lewellen, Thomas K., et al., "Evaluation of a Clinical Scintillation Camera with Pulse Tail Extrapolation Electronics", *The Journal of Nuclear Medicine,* vol. 30, Sep. 1989, pp. 1554–1558.

P. Stentstrom et al., "A New Scalable Modular Data Acquisition System for SPECT (PET)", *IEEE Transactions on Nuclear Science,* vol. 45, No. 3, Jun. 1998, pp. 1117–1121.

International Commission on Radiation, Units and Measurements, "The Poisson Process", *Particle Counting in Radioactivity Measurements,* ICRU Report 52, Bethesda, MD, Nov. 1994, pp. 3–17.

Wong, Wai–Hoi, et al., "A High Count Rate Position Decoding and Energy Measuring Method for Nuclear Cameras Using Anger Logic Detectors", *IEEE Transactions on Nuclear Science,* vol. 45, No. 3, Jun. 1998, pp. 1122–1127.

D.–C. Yu, et al., "Extending the Usable Areas of Modular NaI(Tl) Detector Using Crystal Treatment", *IEEE,* May 1998, 4 pages.

* cited by examiner

RANDOMS CORRECTION USING ARTIFICIAL TRIGGER PULSES IN A GAMMA CAMERA SYSTEM

FIELD OF THE INVENTION

The present invention pertains to the field of nuclear medicine. More particularly, the present invention relates to correcting for random coincidences in a nuclear medicine imaging system capable of coincidence imaging.

BACKGROUND OF THE INVENTION

In nuclear medicine, images of internal structures or functions of the body are acquired by using one or more gamma cameras to detect radiation emitted by a radiopharmaceutical that has been injected into the patient's body. A computer system controls the gamma cameras to acquire data and then processes the acquired data to generate the images. Nuclear medicine imaging techniques include single-photon emission computed tomography (SPECT) and positron emission tomography (PET). SPECT imaging is based on the detection of individual gamma rays emitted from the body, while PET imaging is based on the detection of gamma ray pairs emitted in coincidence in opposite directions due to electron-positron annihilations. Accordingly, PET imaging is sometimes referred to as "coincidence imaging". Nuclear medicine imaging systems, which are sometimes referred to as gamma camera systems, include dedicated SPECT systems, dedicated PET systems, and systems having dual PET/SPECT capability. Gamma camera systems with dual PET/SPECT capability are available from ADAC Laboratories of Milpitas, Calif.

Random coincidences are a factor that affects image quality in coincidence imaging. In coincidence imaging systems, coincidence events may be defined as two events observed by two detectors which occur within a relatively narrow time window. However, a certain fraction of event pairs detected within the time window are not the result of true coincidences (i.e., based on a single positron-electron annihilation) but are based on separate, unrelated annihilation events. Such detected event pairs are referred to as random coincidences, or "randoms". The misinterpretation of randoms as true coincidences produces inaccuracy in the imaging process and, therefore, degrades image quality.

A common approach to randoms correction is to provide a second coincidence timing circuit in parallel with the normal coincidence timing circuit. The second timing circuit includes a time delay on the trigger signal from one detector. The delay is made large enough so that no true coincidence events can be registered by the second timing circuit. Thus, any events which are detected in the second timing circuit can only result from random coincidences. The number and distribution of randoms detected by the parallel timing circuit are proportional to the number and distribution of randoms in the overall coincidence data. As a result, the randoms data can be essentially subtracted from the overall coincidence data.

This approach has a number of disadvantages. For example, it tends to involve a relatively complex hardware solution that adds to the cost and size of the gamma camera system. As radioactivity dosages increase to increase patient throughput, increasingly higher performance is demanded from the coincidence timing circuitry. In addition, since this solution is based on direct measurement of randoms, the effects of deadtime tend to complicate the measurement of randoms. Furthermore, because coincidences in general represent only a small fraction of the overall countrate, the acquired randoms data tends to be noisy.

Another approach to randoms correction is to form an estimate of randoms based upon a mathematical model. Because that approach is based upon only an estimate, however, it is inherently subject to inaccuracies. For example, such an estimate may not take into consideration the spatial variations in randoms. Hence, it is desirable to provide a technique for correcting for randoms in a medical imaging system which overcomes these and other disadvantages of the prior art.

SUMMARY OF THE INVENTION

A method of obtaining a measure of random coincidences in an imaging system including a radiation detector includes using a radiation detector of the imaging system to acquire coincidence data associated with an object. Artificial trigger signals are generated and used to acquire a measure of random coincidences associated with the coincidence data. Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which.

DETAILED DESCRIPTION

A technique for correcting for random coincidences in a gamma camera system using artificial trigger pulses is described. Briefly, the technique is as follows. A gamma camera system includes a processing system coupled to at least two scintillation detectors. Each of the detectors generates event-based trigger pulses in response to scintillation events. Each of the detectors also includes a pulse generator, which generates artificial trigger pulses, i.e., trigger pulses that are not caused by scintillation events. When an artificial trigger pulse in one detector occurs in coincidence with an event-based trigger pulse in the other detector, corresponding event data is registered by the detectors, and the artificial trigger pulse is associated with a predetermined energy level. The processing system receives the data and examines an energy level associated each trigger pulse. Based on the energy level, the processing system identifies any singles events that were part of a coincidence registered in response to an artificial trigger pulse. The processing system thereby prevents such singles events from contributing to the coincidence images and instead uses such singles events to generate a singles image for each detector. The singles images from the detectors are then used to create a randoms image, which is used to correct the coincidence images for random coincidences. The artificial pulse generator in each detector is programmable and can be adjusted in real-time (i.e., during data acquisition) to adjust the pulse rate, pulse width, or both, based on the current measured singles rate.

The described technique is well-suited for use in a gamma camera system capable of both single-photon (SPECT) and coincidence (PET) imaging. Note, however, that this technique can also be used advantageously in a dedicated coincidence (PET) imaging system.

Figure 1:
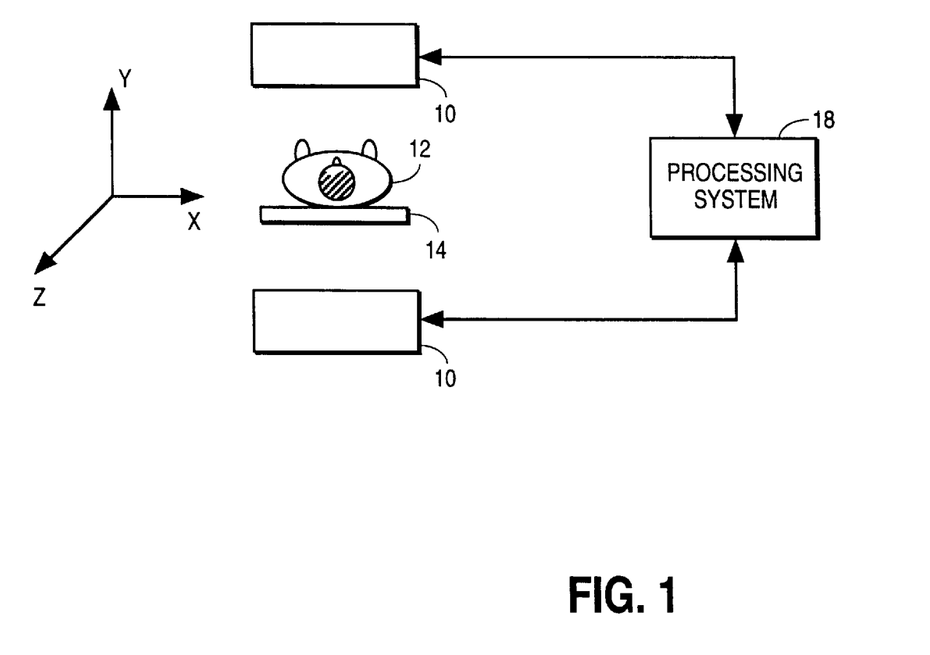
FIG. 1 is a block diagram of a two-detector gamma camera system.

FIG. 1 is a block diagram of a dual-detector gamma camera system capable of both coincidence imaging and single-photon imaging, in which the randoms correction technique can be implemented. Note that the randoms correction technique can also be implemented in systems having a different number of detectors. The system of FIG. 1 includes a processing system 18 coupled to two scintillator-based detectors 10. In one embodiment, each of the detectors 10 includes a single, continuous scintillation crystal, an array of photomultiplier tubes (PMTs) optically coupled to the crystal, and appropriate processing circuitry coupled to receive and process the outputs of the PMTs and to provide the processed outputs to the processing system 18. The detectors 10 are also supported by a gantry that is capable of rotating the detectors 10, either individually or in unison, about an axis of rotation that is perpendicular to the x-y plane (parallel to the z axis). A patient 12 rests on a table 14 positioned between the detectors 10. The detectors 10 are configured for coincidence imaging, i.e., in a 180 degree orientation relative to each other about an axis of rotation that passes through the patient 12 parallel to the z axis.

The processing system 18 controls the overall operation of the gamma camera system, including receiving data acquired by the detectors 10, processing the data, and reconstructing images based on the data. The processing system 18 also controls certain functions of the detectors 10 using various control signals. The processing system 18 may be, or may include, for example, one or more of: a conventional computer system, such as a personal computer (PC), a server and/or workstation, a single-board computer, or a combination of such devices. Note that in alternative embodiments, however, any of the above-mentioned functions of the processing system 18, or aspects thereof, may instead be implemented within the detectors 10, the gantry, or in other distinct modules. Thus, processing system 18 may actually be embodied as multiple distinct processing systems.

Figure 2:
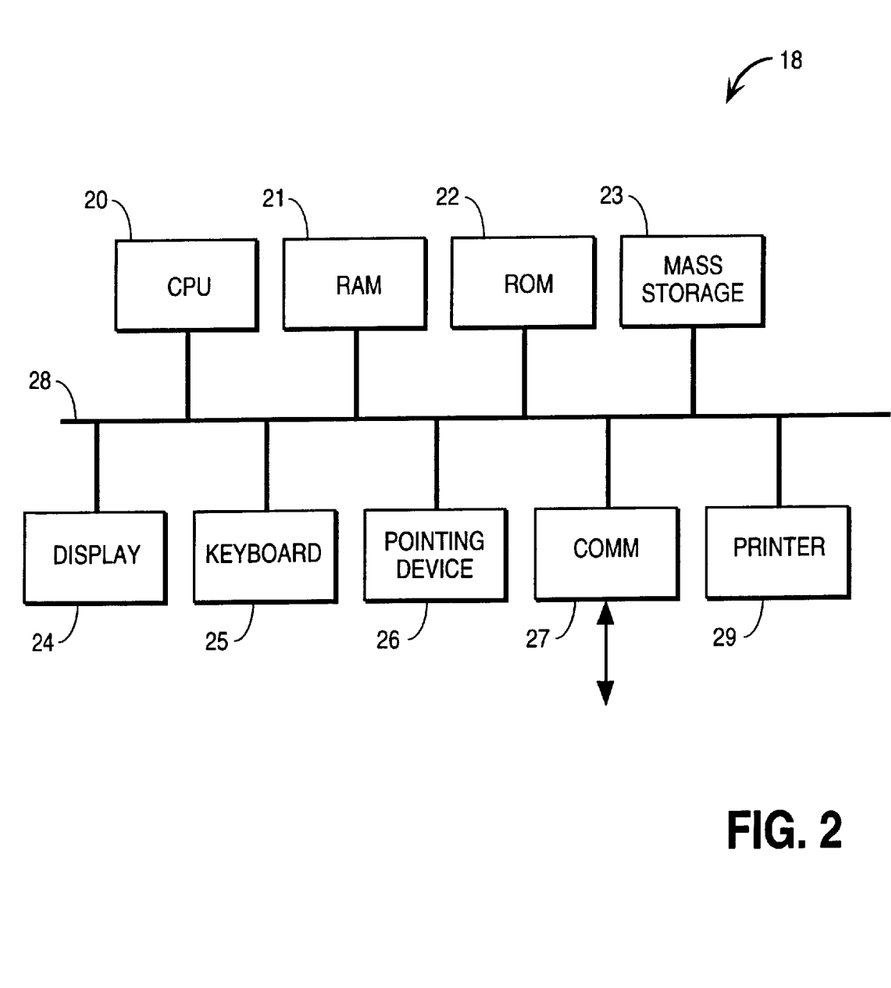
FIG. 2 is a block diagram of the processing system of the gamma camera system of FIG. 1.

FIG. 2 illustrates a block diagram of the processing system 18 according to one embodiment. Note, however, that the specific architecture of processing system 18 is not germane to the present invention. In the illustrated embodiment, the processing system 18 includes a central processing unit (CPU) 20, random access memory (RAM) 21, read-only memory (ROM) 22, and a mass storage device 23, each coupled to a bus system 28. The bus system 28 may represent multiple physical buses coupled together by appropriate bridges, controllers, and/or adapters. Also coupled to the bus system 28 are a display device (including appropriate display controller) 24, which may be a cathode ray tube (CRT), liquid crystal display (LCD), or the like; a keyboard 25; a pointing device 26, such as a mouse, trackball, touchpad, or the like; a data communication device 27; and a printer 29. Data communication device 27 may be used by processing system 18 to communicate with the detectors 10 and/or other computer systems or components and may be, for example, a simple transceiver, a network adapter, modem, or any other suitable data communication device. Display device 24 and printer 29 may be used to display and print, respectively, tomographic images reconstructed by processing system 18.

Note that the randoms correction technique may be embodied, at least in part, in software. That is, the technique may be carried out, at least in part, in a computer system, such as processing system 18, in response to its CPU executing sequences of instructions contained in memory. The instructions may be executed from RAM, ROM, a mass storage device, or a combination thereof. In certain embodiments, hardwired circuitry may be used in place of, or in combination with, software instructions to implement the present invention. Thus, the present invention is not limited to any specific combination of hardware circuitry and software, nor to any particular source of such software.

Figure 3:
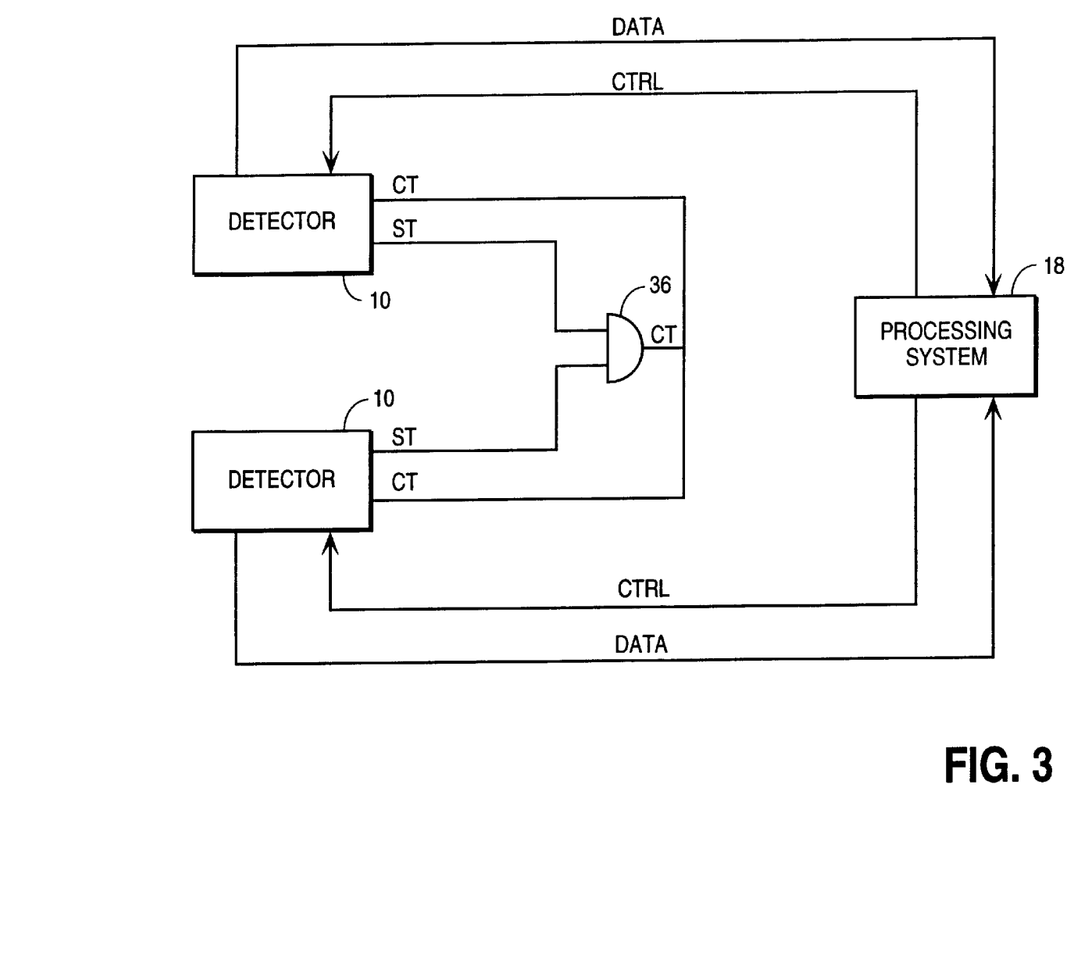
FIG. 3 illustrates the coincidence detection circuitry (CDC) of the gamma camera system of FIG. 1.

FIG. 3 illustrates the coincidence detection circuit of the gamma camera system, which enables the system to detect coincidence events. As shown, each of the detectors 10 outputs trigger pulses via singles trigger signals ST in response to each detected scintillation event. The singles trigger signal ST from each detector is applied to an input of the coincidence detection circuit (CDC) 36, which outputs a coincidence trigger signal CT to each of the detectors 10. The CDC 36 may be a simple AND gate 37, as shown on FIG. 3. When the system is in coincidence mode, each of the detectors 10 responds to assertion of the coincidence trigger signal CT by registering the position and energy of the corresponding scintillation event. When the system is in single-photon mode, each of the detectors 10 registers position and energy data in response to assertion of its singles trigger signal ST; the coincidence trigger signal CT is not used. Position data (i.e., x,y coordinates) and energy data for registered events are provided by each of the detectors 10 to the processing system 18 via the DATA signals. The processing system 18 controls certain functions of the detectors 10 using various control (CTRL) signals. The CTRL signals may include clock signals for controlling data transfers, programming signals for programming variable delays, selecting the imaging mode (PET or SPECT) and other functions, and other signals, the specifics of which are not germane to the present invention.

Figure 4A:
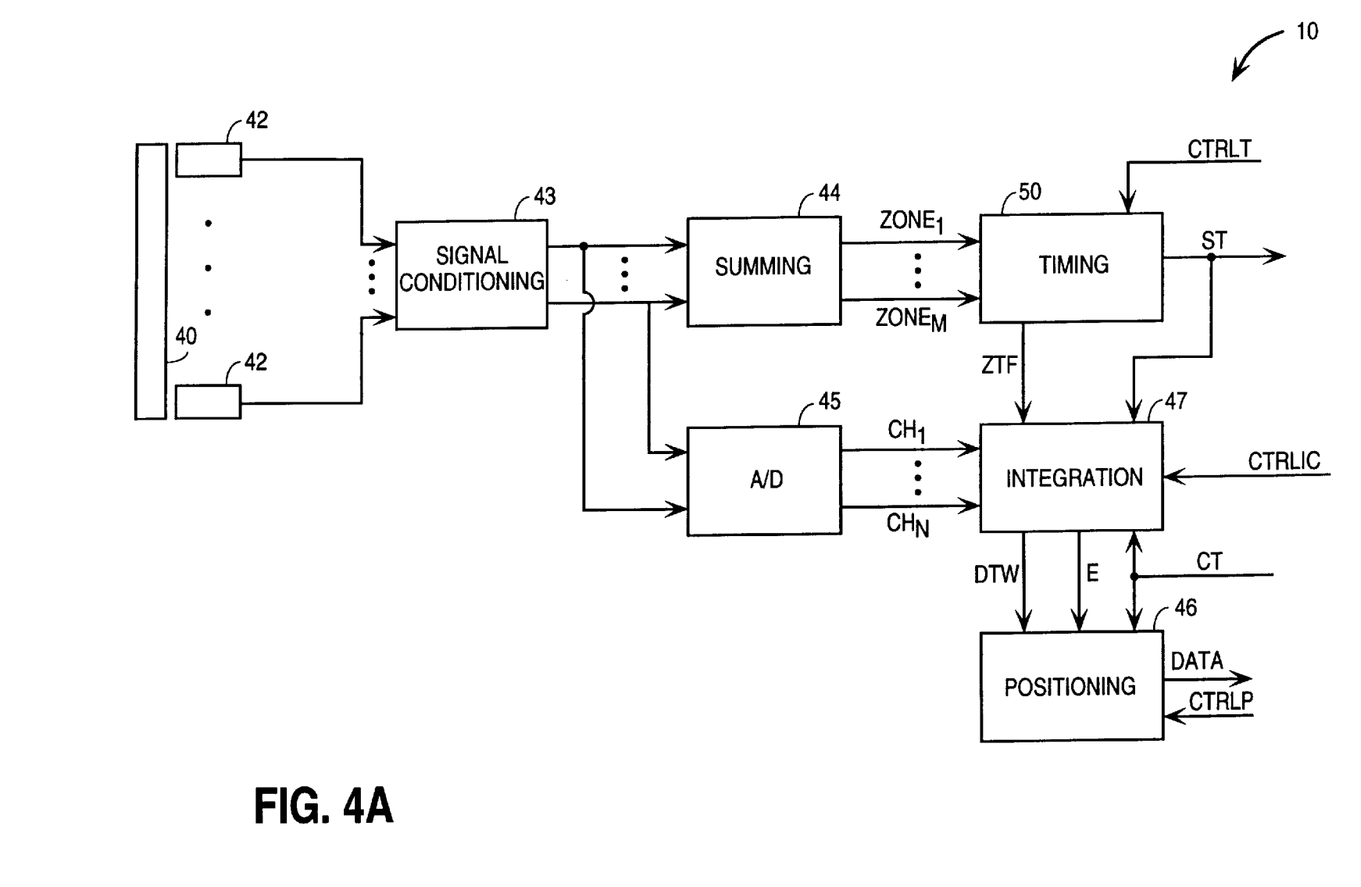
FIG. 4A illustrates the internal components of a detector of the gamma camera system of FIG. 1.

FIG. 4A illustrates the internal components of one of the detectors 10, according to one embodiment. The detectors 10 may be assumed to be identical for purposes of the present invention. The detector 10 includes a scintillation crystal 40, such as a NaI(Tl) crystal, which is optically coupled to a number of PMTs 42. The outputs of the PMTs 42 are applied to signal conditioning circuit 43. The signal conditioning circuit 43 provides amplification and normalization of the PMT outputs and, if needed, other types of signal conditioning. The signal conditioning circuit 43 outputs, for each PMT output, a separate amplified signal to both summing network 44 and to analog-to-digital (A/D) circuit 45. The A/D circuit 45 converts the amplified PMT outputs to digital values, which are provided as channel signals $CH_i$, to integration circuitry 47 (i=1, 2, ..., N, where N is the number of PMTs in the detector).

In general, integration circuitry 47 integrates event pulses in the channel signals $CH_i$ to produce integrated energy (E) values, which are provided to positioning circuitry 46. Integration circuitry 47 also generates a digital trigger word (DTW) signal, which is also provided to positioning circuitry 46. Further, integration circuitry 47 corrects for pre-pulse pile-up and performs pulse tail extrapolation. Integration circuitry 46 may be controlled, at least in part, by integration control signals CTRLIC from processing system 18, which are a subset of the above-mentioned CTRL signals.

Positioning circuitry 46 computes position (x,y) coordinates associated with scintillation events. In response to assertion of the coincidence trigger CT from the CDC 36, positioning circuitry 46 registers the position and energy (E) data for a corresponding scintillation event and provides the data to the processing system 18 via the DATA signal. Positioning circuitry 46 may be controlled, at least in part, by position control signals CTRLP from processing system 18, which are a subset of the CTRL signals.

Figure 5:
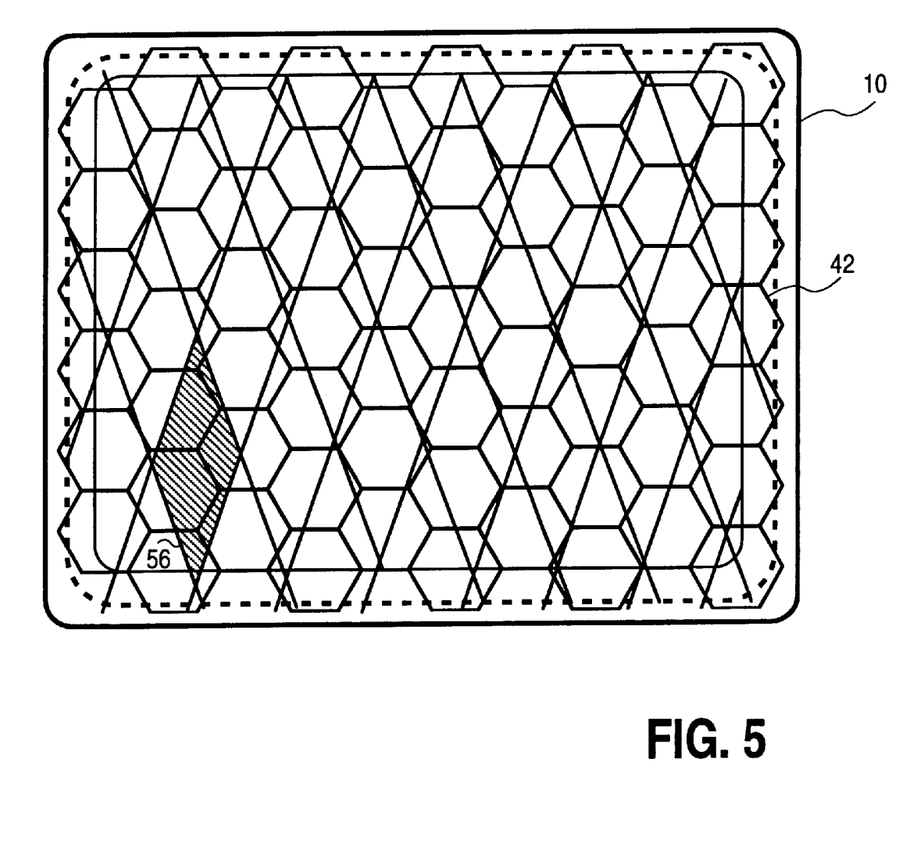
FIG. 5 illustrates a detector imaging surface divided into a number of zones.

The imaging surface of each of the detectors 10 is divided into a number of timing zones. Each timing zone includes a subset of the array PMTs 42. FIG. 5 illustrates the imaging surface of a detector 10, and an example of how the imaging surface may be divided into timing zones. One timing zone 56 is shaded for purposes of illustration. Note that many variations are possible in the number and shape of the timing zones, for purposes of the present invention. That is, the particular number of zones, the zone shapes, and the zone arrangements are not germane to the present invention.

Thus, referring again to FIG. 4A, the summing network 44 receives the amplified outputs of the individual PMTs from the signal conditioning circuit 43 and sums the amplified outputs to generate one output $ZONE_j$ for each timing zone (j=1, 2, ..., M, where M is the number of timing zones on the detector). Summing network 44 then provides each zone output $ZONE_j$ to timing circuitry 50. Timing circuitry 50 applies a signal-level threshold function to the zone outputs $ZONE_j$ and, for the zone outputs $ZONE_j$ that meet the threshold level, generates pulses of singles trigger ST signal. Timing circuitry 50 also generates a zone trigger function (ZTF) signal in response to each scintillation event which meets the threshold level, which is provided to integration circuitry 47. The ZTF signal is a multi-bit digital value, i.e., one bit for each PMT in the detector. The state of each ZTF bit at any given point in time indicates whether the corresponding PMT is affected by the most recently detected scintillation event. Note that timing circuitry 50 may be controlled, at least in part, by timing control signals CTRLT from processing system 18, which represent a subset of the CTRL signals.

Figure 4B:
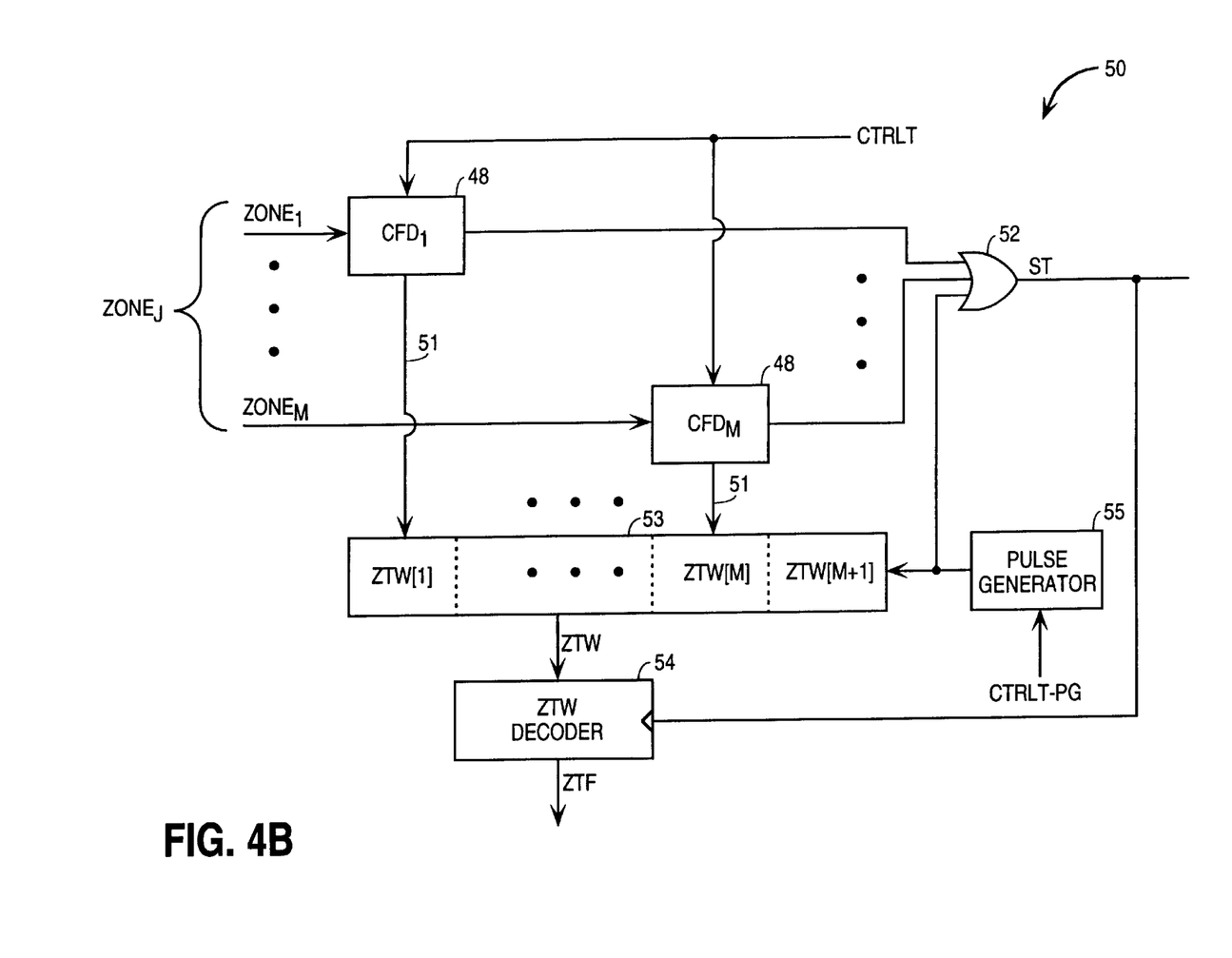
FIG. 4B illustrates the timing circuitry of the detector, including a pulse generator for generating artificial trigger pulses.

FIG. 4B illustrates the timing circuitry 50 in greater detail. Timing circuitry 50 includes a number of constant fraction discriminators (CFDs) 48, i.e., one CFD 48 for each timing zone. Each of the zone outputs $ZONE_j$ is applied as input to a corresponding CFD 48. The CFDs 48 each provide amplitude independent triggering to maintain tight timing tolerances. The details of the CFDs are not germane to the present invention. Each CFD 48 provides an output signal to an OR gate 52. The output of OR gate 52 is the trigger signal ST from the detector 10, which is applied to CDC 36 (FIG. 3). Each CFD 48 also outputs a signal 51 to ZTW register 49; each such signal 51 determines the state of a corresponding bit of ZTW register 49. Thus, the ZTW register 53 includes one bit for each timing zone, and one additional bit which will be discussed below. The state of the ZTW value identifies the particular zones that responded to a scintillation event during each timing cycle. The output ZTW value of the ZTW register 53 is applied to ZTW decoder 54. ZTW decoder 54 maps the ZTW value to individual PMTs; that is, ZTW decoder 54 determines which PMT channels are represented by each ZTW value. The mapping function is based on knowledge of which PMTs are included within each timing zone and the well-known light spread function (LSF). The output of ZTW decoder 54 is signal ZTF, which includes one bit for each PMT channel and a bit associated with programmable pulse generator 55. Signal ZTF is provided to integration circuitry 47 (FIG. 4A), as noted above.

As noted above, the randoms correction technique involves correcting for randoms by generating a singles image for each detector. The CDC 36 generates the coincidence trigger signal CT only in response to coincidental assertion of the singles triggers ST from both detectors. However, the inclusion of programmable artificial trigger pulse generator 55 in the timing circuitry 50 of each detector enables each detector to register singles events during coincidence imaging, in order to generate a singles image for each detector. The output of pulse generator 55 is applied to an input of OR gate 52. In addition, the output of pulse generator 55 is used to determine the state of bit ZTW[M+1] of ZTW register 53.

Certain ones of the artificial trigger pulses generated by pulse generator 55 will coincide with event-based trigger pulses in the other detector. These artificial trigger pulses enable the CDC 36 to generate a coincidence trigger CT in response to the event-based trigger pulses, which would otherwise be ignored when the imaging system is in coincidence mode.

The state of bit ZTW[M+1] is used to indicate timing cycles in which an artificial trigger pulse was generated by pulse generator 55. This bit is decoded by ZTW decoder 54, and the information is passed on to the integration circuitry 47 in the ZTF signal. The integration circuitry 47 interprets the ZTF signal and, as noted above, assigns a predetermined energy value to data associated with artificial trigger pulses.

Still referring to FIG. 4B, pulse generator 55 receives an input CTRLT-PG from the processing system 18 to program the rate and/or the pulse width of the artificial trigger pulses. Signal CTRLT-PG may be a subset of the CTRLT signals. The pulse generator 55 may be a simple loadable binary counter. The pulse rate or width may be selected in order to optimize operation in view of the current measured singles rate an any given point in time during data acquisition. For example, if it is desired to maintain a constant number of counts in the randoms image, a higher measured singles rates might warrant a lower artificial pulse rate. The actual programmed rates and/or pulse widths may be determined based on empirical data. Each detector 10 includes a rate meter (not shown) for measuring the singles rate in response to the artificial trigger pulses. Note that the singles rate measured as a result of artificial trigger pulses is proportional to the true singles rate.

Thus, it will be recognized that an advantage of the randoms correction technique described above is that singles data for randoms correction can be acquired simultaneously with the acquisition of coincidence data. Consequently, in a dual-mode PET/SPECT system, there is no need to switch between coincidence mode and single-photon mode, which can be time consuming. In addition, there is no need to provide increasingly higher-performance hardware to accommodate higher countrates. Furthermore, the acquired singles data represents the spatial dependency of randoms.

Figure 6:
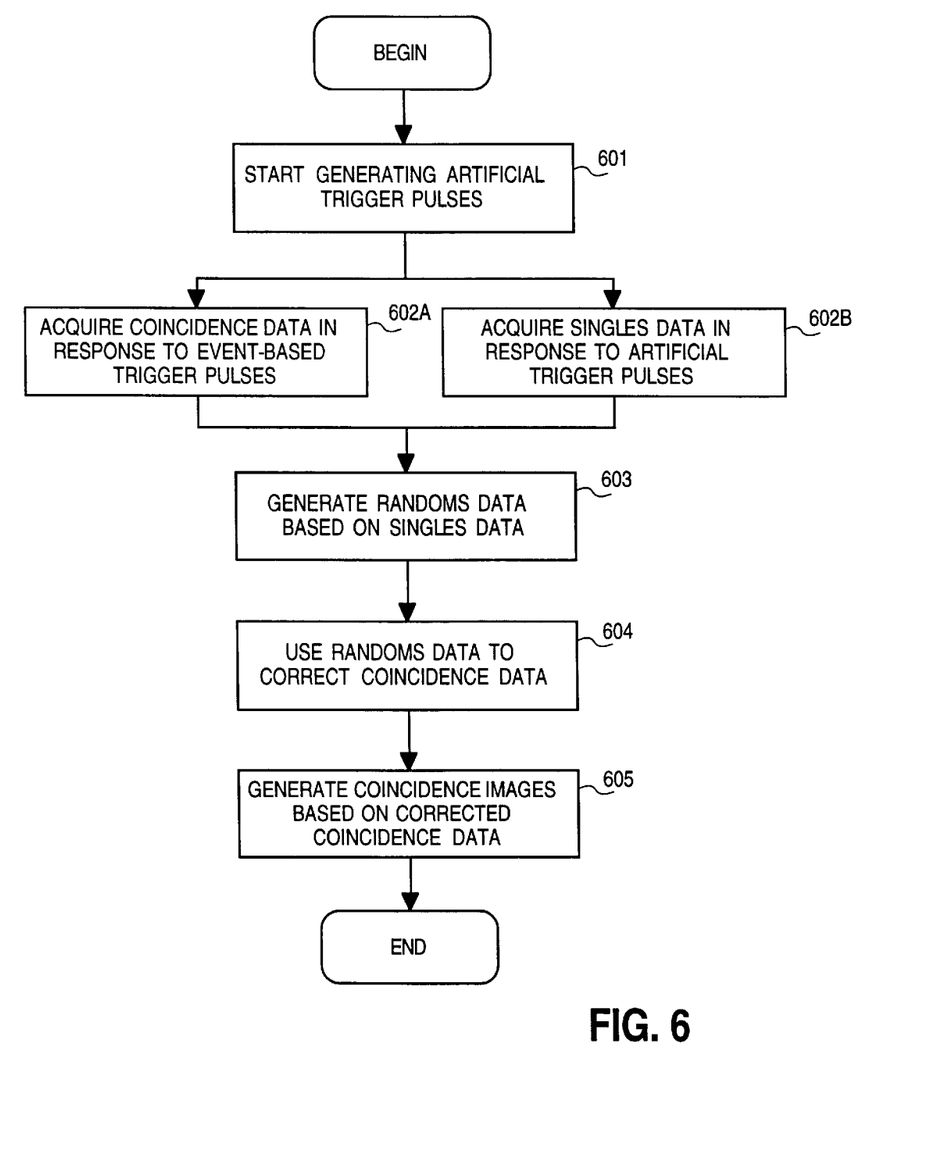
FIG. 6 is a flow diagram illustrating a routine for performing randoms correction by acquiring singles data using an artificial trigger pulse generator.

FIG. 6 illustrates a routine for generating randoms data based upon artificial trigger pulses and correcting the coincidence data based on the randoms data. The pulse generator 55 in each detector is initially programmed with a periodic rate and/or pulse width, which may initially be default values or, as noted above, they may be based upon the measured singles rate. The imaging session begins by initiating the generation of artificial trigger pulses at 601. Next, coincidence data is acquired at 602A in response to event-based trigger pulses concurrently with the acquisition of singles data at 602B in response to artificial trigger pulses. After a complete set of data is acquired, randoms data is generated based upon the singles data at 603. The randoms data may be in the form of an image or a sinogram. At 604, the randoms data is then used to correct corresponding coincidence data for random coincidences, and at 605, coincidence images are generated based upon the corrected coincidence data.

Figure 7:
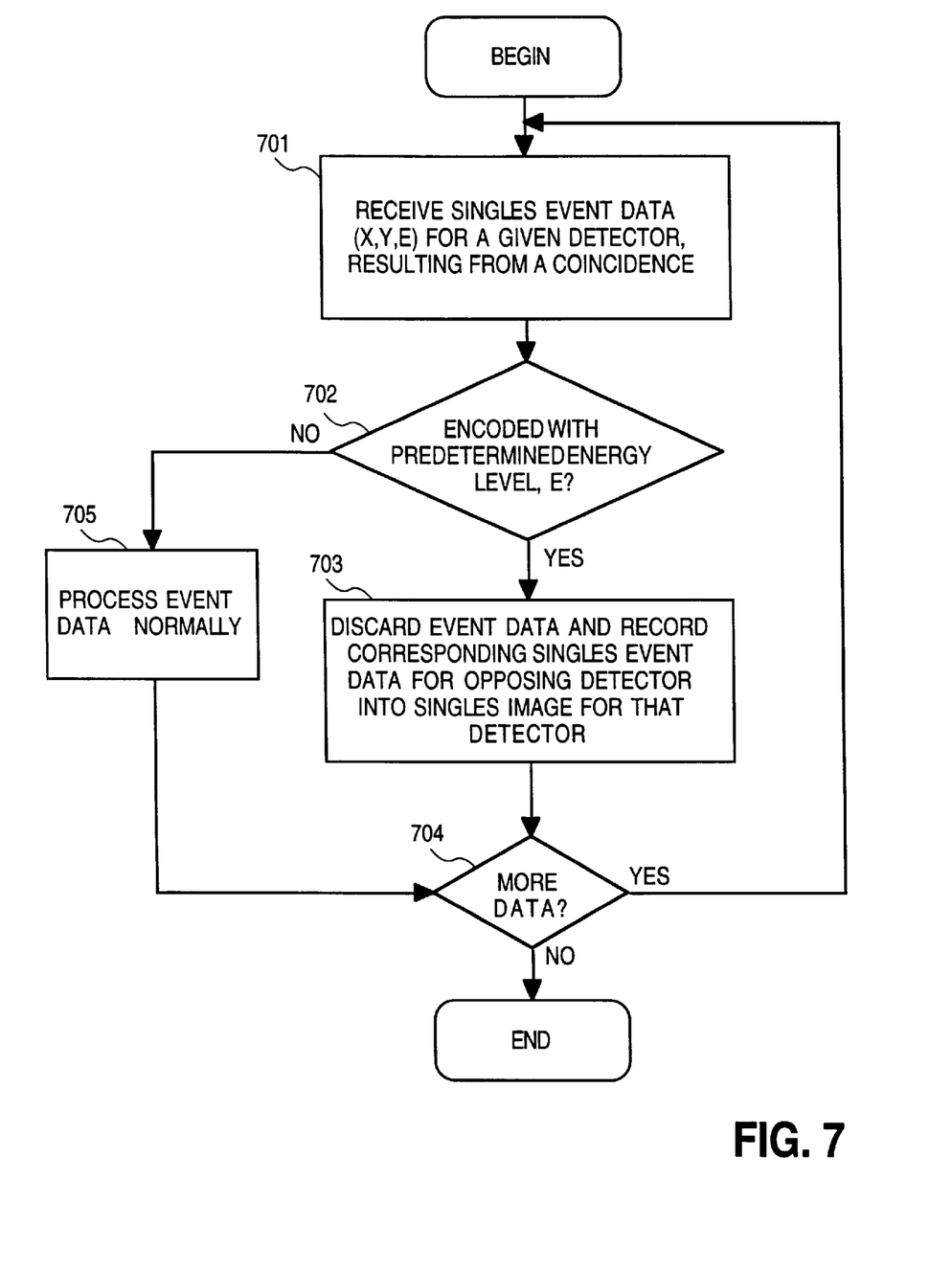
FIG. 7 is a flow diagram illustrating a routine for identifying singles events registered in response to artificial trigger pulses.

FIG. 7 illustrates a routine that can be implemented in the processing system 18 to distinguish between data corresponding to artificial trigger pulses and actual event data (i.e., data resulting from real coincidence pairs). At 701, the processing system 18 receives position (x-y) and energy data from a given detector resulting from a coincidence. The coincidence may have been based on a pair of actual scintillation events or only one scintillation event paired with an artificial trigger pulse. Hence, at 702, it is determined whether the energy level encoded in the received data is the predetermined energy level, mentioned above. If so, the data corresponds to an artificial trigger pulse. Accordingly, at 703, such data is discarded, and the corresponding data from the opposing detector is recorded into a singles image for that detector. If the energy level in the received data was not the predetermined energy level at 702, then at 705 the data is processed normally as coincidence data. Following 703, if there is additional data to be processed from the detectors (704), then the routine repeats from 701; otherwise the routine ends.

Figure 8:
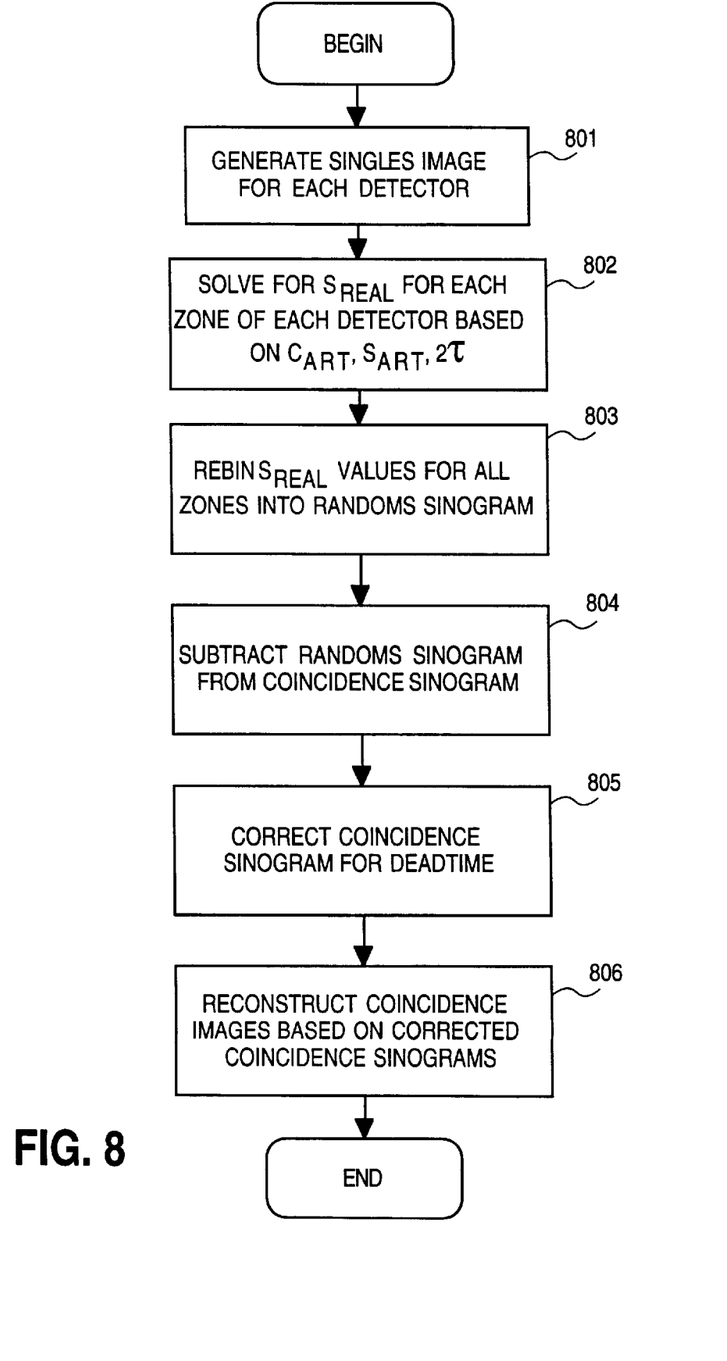
FIG. 8 is a flow diagram illustrating a routine for generating singles images using artificial trigger pulses and for correcting coincidence data using the singles images.
Figure 9:
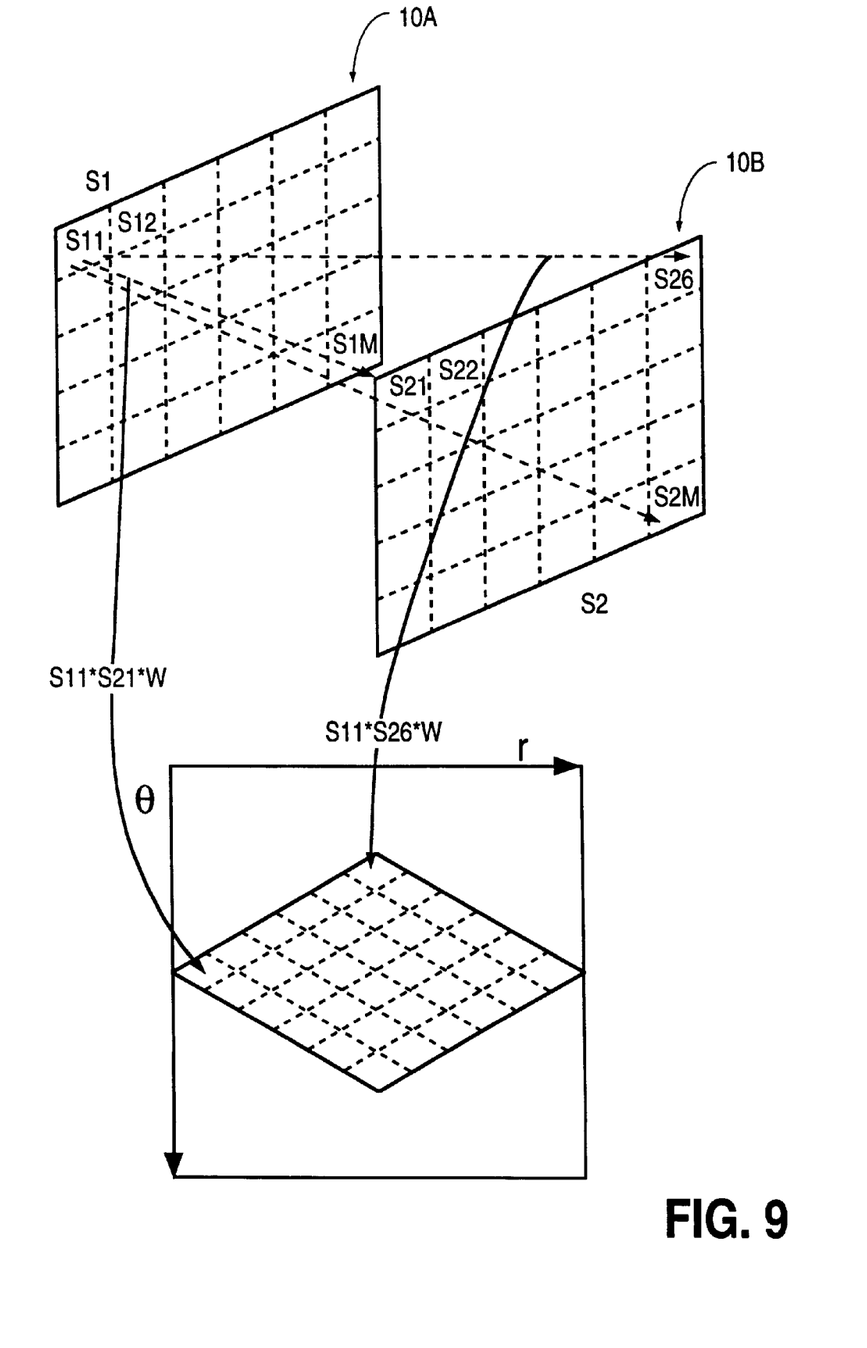
FIG. 9 illustrates zones of two detectors of a gamma camera system and a corresponding randoms sinogram.

When the data received by the processing system 18 from the detectors are rebinned, some portion of that data will be based on artificial trigger pulses. The spatial density of these events is directly related to the singles rate for each detector. In particular, the coincidence rate that is measured as a result of artificial trigger pulses can be represented as a function of the real singles rate and the singles rate measured as a result of the artificial trigger pulses according to the equation:

$$C_{art}(\text{detector}, x,y) = S_{real}(\text{detector}, x,y) \cdot S_{art} \cdot 2\tau$$

where $C_{art}$ is the measured coincidence rate, $S_{real}$ is the real singles rate, $S_{art}$ is the rate of artificial trigger pulses, and $2\tau$ is the duration of the coincidence timing window, which is twice the duration of a trigger pulse caused by a given event. Since $C_{art}$ is measured and since $S_{art}$ and $2\tau$ are known, the above equation can be solved for $S_{real}$. The spatial distribution of singles events across each detector can be calculated and combined to form a randoms sinogram, as will now be described with reference to FIGS. 8 and 9.

At 801, a singles image is generated for each detector. At 802, the processing system 18 solves for the value $S_{real}$ for each timing zone of each detector based upon the values $C_{art}$, $S_{art}$ and $2\tau$ as set forth in the equation above. Next, at 803, the $S_{real}$ values for all zones are rebinned into a randoms sinogram, in a manner which will be described below. At 804, the randoms sinogram is subtracted from the coincidence sinogram, and at 805, if desired, the coincidence sinogram is corrected for deadtime. A conventional deadtime correction technique may be used. At 806, the corrected coincidence sinograms are used to reconstruct coincidence images.

A process for generating a randoms image from the acquired singles data will now be described. In general, randoms R can be calculated according to the equation $R = S1 \cdot S2 \cdot 2\tau$ where S1 represents the (real) singles rate from one detector, S2 represents the (real) singles rate from the other detector, and $2\tau$ represents the duration of the coincidence timing window. As noted above, each of the detectors 10 is divided into multiple timing zones, each of which may include multiple PMTs and/or portions thereof. Associated with each zone is a singles rate that is a subset of the overall singles rate (S1 or S2) for the detector. For example, referring to FIG. 9, the total singles rate S1 for one of the detectors 10A can be expressed as S1=S11+S12+S13+ . . . +S1M. Similarly, the total singles rate S2 for the other detector 10B can be expressed as S2=S21+S22+S23+ . . . +S2M. Therefore, the total randoms R can be expressed as:

$$R = (S11+S12+ \ldots +S1M) \cdot (S21+S22+ \ldots +S2M) \cdot 2\tau$$
$$= (S11 \cdot S21 + S11 \cdot S22 + \ldots + S1M \cdot S2M) \cdot 2\tau$$
$$= R1 + R2 + \ldots + R(M \cdot M)$$

where $R_k$ (k=1, 2, . . . , (M·M)) is the randoms detected by any pair of zones that consists of a zone from one detector and a zone from the other detector. Thus, the above equation represents the concept that the global randoms are simply the sum of all the randoms contributed by each pair of zones from the two detectors.

By applying the above concept, a randoms image can be obtained, which can be used to subtract out the randoms from the coincidence image. FIG. 9 illustrates how the singles rate data is rebinned into a randoms sinogram. As noted above, each of the detectors is divided into n zones—specifically, detector 10A is divided into zones S11, S12, . . . S1M, and detector 10B is divided into zones S21, S22, . . . S2M. Counts detected by each detector are rebinned into a randoms sinogram 60. For each detector angle about the z axis, the rebinned data appears as a diamond in the randoms sinogram. The final random sinogram is a summation of all the individual sinograms for each axial position and is used to generate the randoms image. The single-slice rebinning technique may be used in the axial direction. The randoms image is then subtracted from the coincidence image.

Thus, a technique for correcting for random coincidences in a gamma camera system using artificial trigger pulses has been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative sense rather than a restrictive sense.

What is claimed is:

1. A method of obtaining a measure of random coincidences in an imaging system including a radiation detector, the method comprising:
   using the radiation detector to acquire coincidence data of an object to be imaged;
   generating a plurality of artificial trigger signals; and
   using the plurality of artificial trigger signals to acquire a measure of random coincidences associated with the coincidence data.

2. A method according to claim 1, wherein generating the plurality of artificial trigger signals comprises injecting a plurality of artificial trigger pulses into a stream of real trigger pulses, wherein only the real trigger pulses are based on radiation induced events.

3. A method according to claim 2, wherein generating the plurality of artificial trigger pulses comprises generating the plurality of artificial trigger pulses at a selected rate, the method further comprising adjusting the selected rate based on a current singles rate associated with the detector.

4. A method according to claim 2, wherein generating the plurality of artificial trigger pulses comprises selecting a pulse width for the plurality of artificial trigger pulses based on a current singles rate associated with the detector.

5. A method according to claim 2, wherein using the plurality of artificial trigger pulses to acquire a measure of random coincidences comprises:
   using the plurality of artificial trigger pulses to acquire a singles image; and
   using the singles image to determine the measure of random coincidences.

6. A method of using a gamma camera system to generate an image of an object corrected for random coincidences, the method comprising:
   generating a plurality of event-based trigger pulses in response to scintillation events associated with the object;
   generating a plurality of artificial trigger pulses;
   acquiring coincidence data of the object based on the event-based trigger pulses;
   acquiring randoms data representing random coincidences based on the artificial trigger pulses;
   using the randoms data to correct the coincidence data; and
   generating the image of the object based on the corrected coincidence data.

7. A method according to claim 6, wherein generating the plurality of artificial trigger pulses comprises generating the plurality of artificial trigger pulses at a selected rate based on a current measured singles rate.

8. A method according to claim 6, wherein generating the plurality of artificial trigger pulses comprises selecting a pulse width for the plurality of artificial trigger pulses based on a current measured singles rate.

9. A method according to claim 6, wherein acquiring randoms data based on the artificial trigger pulses comprises:
   using the plurality of artificial trigger pulses to acquire a singles image associated with the object; and
   using the singles image to acquire the measure of random coincidences.

10. A method according to claim 6, wherein the gamma camera system includes a pair of gamma radiation detectors, and wherein generating the plurality of event-based trigger pulses comprises independently generating a plurality of event-based trigger pulses for each of the detectors; and wherein generating the plurality of artificial trigger pulses comprises independently generating the plurality of artificial trigger pulses for each of the detectors.

11. A method according to claim 10, further comprising:
   combining the artificial trigger pulses with the event-based trigger pulses to produce a single pulse stream for each of the detectors; and
   generating a coincidence trigger in response to each of a plurality of coincidental pairs of trigger pulses, each coincidental pair of trigger pulses including one trigger pulse from the single pulse stream of each of the pair of detectors.

12. A method according to claim 11, further comprising associating a predetermined energy level with each coincidental pair of trigger pulses that is based on an artificial trigger pulse.

13. A method of correcting for random coincidences in a medical imaging system, the medical imaging system including a pair of detectors, each of the detectors for detecting scintillation events associated with an object to be imaged, the method comprising:
   using each of the detectors to generate a trigger pulse in response to each scintillation event detected by said detector to produce a plurality of event-based trigger pulses;
   using each of the detectors to generate a plurality of artificial trigger pulses at a selected rate; and
   combining the artificial trigger pulses with the event-based trigger pulses to produce a pulse stream for each of the detectors;
   generating a coincidence trigger in response to each of a plurality of coincidental pairs of trigger pulses, each coincidental pair of trigger pulses including one trigger pulse from the pulse stream of each of the detectors, the coincidental pairs of trigger pulses representing true coincidences, event-based random coincidences, and artificial random coincidences, each artificial random coincidence representing a singles event associated with one of the artificial trigger pulses;
   causing each of the detectors to register an event in response to each coincidence trigger;
   identifying the ones of the coincidence triggers which correspond to artificial random coincidences;
   for each identified coincidence trigger which corresponds to an artificial random coincidence, updating a singles image for one of the detectors based on a registered singles event associated with said identified artificial random coincidence, to generate a singles image for each of the detectors;
   generating a randoms image based on the singles images for the detectors;
   forming a coincidence image of the object; and
   using the randoms image to correct the coincidence image for random coincidences.

14. A method according to claim 13, further comprising adjusting the rate at which the artificial trigger pulses are generated for one of the detectors based on a current singles rate of said one of the detectors.

15. A method according to claim 13, further comprising selecting a pulse width for the artificial trigger pulses based on a current singles rate of one of the detectors.

16. A method according to claim 13, wherein said identifying comprises:
   for each coincidence trigger that corresponds to an artificial random coincidence, associating a predetermined energy level with a singles event corresponding to said coincidence trigger; and
   distinguishing singles events associated with artificial coincidences from singles events associated with true coincidences or event-based random coincidences based on energy levels associated with each of said singles events.

17. A gamma camera imaging system comprising:
   means for generating a plurality of event-based trigger signals in response to scintillation events associated with the object;
   means for generating a plurality of artificial trigger signals;
   means for acquiring coincidence data of the object based on the event-based trigger signals;

means for acquiring randoms data representing random coincidences based on the artificial trigger signals;

means for using the randoms data to correct the coincidence data; and means for generating the image of the object based on the corrected coincidence data.

18. A gamma camera system according to claim 17, wherein the means for generating the plurality of artificial trigger pulses comprises means for generating the plurality of artificial trigger pulses at a selected rate, the gamma camera system further comprising further comprising means for selecting the rate based on a current measured singles rate.

19. A gamma camera system according to claim 17, wherein the means for generating the plurality of artificial trigger pulses comprises means for generating the plurality of artificial trigger pulses with a selected pulse width, the gamma camera system further comprising further comprising means for selecting the pulse width based on a current measured singles rate.

20. A gamma camera system according to claim 17, wherein the means for acquiring randoms data based on the artificial trigger pulses comprises:

means for using the plurality of artificial trigger pulses to acquire a singles image associated with the object; and means for using the singles image to acquire the measure of random coincidences.

21. A gamma camera system according to claim 17, further comprising a pair of gamma radiation detectors, wherein the means for generating the plurality of event-based trigger pulses comprises means for independently generating a plurality of event-based trigger pulses for each of the detectors, and wherein the means for generating the plurality of artificial trigger pulses comprises means for independently generating the plurality of artificial trigger pulses for each of the detectors.

22. A gamma camera system according to claim 21, further comprising:

means for combining the artificial trigger pulses with the event-based trigger pulses to produce a single pulse stream for each of the detectors; and means for generating a coincidence trigger in response to each of a plurality of coincidental pairs of trigger pulses, each coincidental pair of trigger pulses including one trigger pulse from the single pulse stream of each of the pair of detectors.

23. A gamma camera system according to claim 21, further comprising means for identifying a plurality of singles events that are registered in response to the artificial trigger pulses by associating a predetermined energy level with each of said singles events.

24. A nuclear medicine imaging system comprising:

a plurality of scintillation detectors, each of the scintillation detectors configured to generate a plurality of event-based trigger pulses in response to scintillation events and a plurality of artificial trigger pulses and configured to combine the event based trigger pulses and the artificial trigger pulses into a combined trigger signal;

a coincidence detection circuit coupled to receive the combined trigger signal from each of the detectors and configured to cause each of the detectors to register an event in response to coincidences between the combined trigger signals of the dectors; and a processing system coupled to the detectors and configured to acquire randoms data representing random coincidences based on the artificial trigger pulses, to acquire coincidence data of the object, to correct the coincidence data based on the randoms data, and to form images of the object based on the corrected coincidence data.

25. A nuclear medicine imaging system according to claim 24, wherein each of the detectors comprises:

a trigger circuit for generating the plurality of event-based trigger pulses; and a programmable pulse generator for generating the plurality of artificial trigger pulses at a programmed rate, wherein the programmed rate is based on a current measured singles rate.

26. A nuclear medicine imaging system according to claim 24, wherein each of the detectors comprises:

a trigger circuit for generating the plurality of event-based trigger pulses; and a programmable pulse generator for generating the plurality of artificial trigger pulses using a programmed pulse width, wherein the programmed pulse width is based on a current measured singles rate.

27. A nuclear medicine imaging system according to claim 24, further comprising a logic circuit for combining the event based trigger pulses and the artificial trigger pulses into the combined trigger signal.

28. A nuclear medicine imaging system according to claim 24, wherein each detector is further configured to associate a predetermined energy level with each said event that results from one of the artificial trigger signals.

29. A nuclear medicine imaging system according to claim 24, wherein the processing system is further configured to acquire the randoms data based on the artificial trigger pulses by using coincidences detected based on the artificial trigger pulses to acquire a singles image for each of the detectors, and further by using the singles image from each detector to generate the randoms data.

30. A gamma camera based medical imaging system comprising:

plurality of scintillation detectors, each of the detectors including:

a trigger circuit configured to generate event-based trigger pulses in response to scintillation events; and a pulse generator configured to generate artificial trigger pulses;

a coincidence detection circuit coupled to receive, from each of the detectors, a combined pulse stream including event-based trigger pulses and artificial trigger pulses, the coincidence detection circuit outputting a coincidence trigger signal in response to coincidences between the combined pulse stream from each of detector;

wherein each of the detectors is configured to:

register an event in response to receiving the coincidence trigger signal; and tag each registered event that is based on one of the artificial trigger pulses to produce a plurality of tagged events; and a processing system coupled to receive data representing the events registered by each of the detectors, wherein the processing system is configured to:

distinguish the tagged events from events that have not been tagged;

generate a singles image for each of the detectors based on the data representing the tagged events;

generate a randoms image based on the singles image from each of the detectors;

generate a coincidence image based on the data representing events that have not been tagged; and correct the coincidence image based on the randoms image.

31. A gamma camera based medical imaging system according to claim 30, wherein each of the detectors is further configured to tag each registered event that is based on one of the artificial trigger pulses by associating a predetermined energy level with each said event.

32. A method of obtaining a measure of random coincidences in an imaging system including a plurality of radiation detectors, the method comprising:

using the radiation detectors to acquire singles data associated with an object simultaneously with using the radiation detectors to acquire coincidence data associated with the object, by generating a plurality of artificial trigger signals to acquire the singles data; and using the singles data to acquire a measure of random coincidences associated with the coincidence data.

33. A method according to claim 32, wherein generating the plurality of artificial trigger signals comprises combining a plurality of artificial trigger pulses with a plurality of event-based trigger pulses.

* * * * *